(12) United States Patent
Brock et al.

(10) Patent No.: US 7,935,539 B2
(45) Date of Patent: May 3, 2011

(54) GENERIC METHOD FOR LATEX AGGLUTINATION ASSAYS

(75) Inventors: David Brock, Elkhart, IN (US); Jim Mattler, Foxboro, MA (US); Gary Rheinheimer, Goshen, IN (US)

(73) Assignee: Siemens Healthcare Diagnostics, Inc., Tarrytown, NY (US)

( * ) Notice: Subject to any disclaimer, the term of this patent is extended or adjusted under 35 U.S.C. 154(b) by 2082 days.

(21) Appl. No.: 10/367,528

(22) Filed: Feb. 14, 2003

(65) Prior Publication Data

US 2004/0161863 A1 Aug. 19, 2004

(51) Int. Cl.
*G01N 33/553* (2006.01)
*G01N 33/543* (2006.01)

(52) U.S. Cl. .................................. 436/525; 436/518

(58) Field of Classification Search ............ 436/509, 436/534, 805, 815, 825, 525, 523, 518, 517, 436/528, 529, 531, 535, 513, 512; 435/7.5, 435/7.1, 7.9, 7.92, 7.94, 7.95, 965
See application file for complete search history.

(56) References Cited

U.S. PATENT DOCUMENTS

| | | | |
|---|---|---|---|
| 3,171,783 A | 3/1965 | Fisk | |
| 4,427,781 A * | 1/1984 | Masson et al. | 436/509 |
| 4,469,797 A | 9/1984 | Albarella | 436/536 |
| 4,536,479 A | 8/1985 | Vander-Mallie | |
| 4,540,660 A * | 9/1985 | Harte et al. | 435/5 |
| 4,720,455 A * | 1/1988 | Babu et al. | 435/7.93 |
| 4,829,011 A | 5/1989 | Gibbons | |
| 5,100,805 A * | 3/1992 | Ziege et al. | 436/517 |
| 5,236,826 A | 8/1993 | Marshall | |
| 5,252,459 A * | 10/1993 | Tarcha et al. | 435/6 |
| 5,486,452 A * | 1/1996 | Gordon et al. | 435/5 |
| 5,501,949 A | 3/1996 | Marshall | |
| 5,583,003 A * | 12/1996 | Hillyard et al. | 435/7.25 |
| 5,585,278 A | 12/1996 | Vunnam et al. | |
| 5,620,860 A | 4/1997 | Jacobs et al. | 435/7.9 |
| 5,620,861 A | 4/1997 | Cerelli et al. | 435/7.9 |
| 5,654,159 A * | 8/1997 | Allard et al. | 435/7.4 |
| 5,736,344 A | 4/1998 | Kung et al. | 435/7.9 |
| 5,750,411 A * | 5/1998 | Sommer | 436/525 |
| 6,093,546 A * | 7/2000 | Ledden et al. | 435/7.1 |
| 6,645,732 B2 * | 11/2003 | Faatz et al. | 435/7.5 |
| 6,905,882 B2 * | 6/2005 | Buechler | 436/180 |

FOREIGN PATENT DOCUMENTS

| | | |
|---|---|---|
| EP | O 170 302 | 2/1986 |
| JP | 57-206859 | 12/1982 |
| JP | 59-180362 | 10/1984 |
| JP | 03-9156369 | 4/1991 |
| JP | 9-318627 | 12/1997 |
| JP | 10-062421 | 3/1998 |
| JP | 11-133023 | 5/1999 |
| JP | 2001-337092 | 12/2001 |

OTHER PUBLICATIONS

EPO Communication, Nov. 23, 2006.
Stivers, C.R., et al. Development of a urine deoxypyridinoline assay for the Abbott IMX (R) System: Clinical chemistry, American Association for Clinical Chemistry, Washington, D.C. US, vol. 43, No. 6, 1997, p. S173.
Poncelet S M, et al. "Immunoassay of theophylline by latex particle counting" Journal of Immunoassay, vol. 11, No. 1, 1990, pp. 77-88.

* cited by examiner

*Primary Examiner* — Jacob Cheu
*Assistant Examiner* — Pensee T Do
(74) *Attorney, Agent, or Firm* — Noam R. Pollack

(57) ABSTRACT

An improved agglutination immunoassay is characterized by reacting a sample fluid which may contain an analyte with a generic antibody conjugated to latex particles and then adding an antibody specific to the analyte to be determined. Agglutination resulting from adding the antibody specific to the analyte is measured and correlated with the amount of analyte in the sample.

9 Claims, No Drawings

GENERIC METHOD FOR LATEX AGGLUTINATION ASSAYS

BACKGROUND OF THE INVENTION

This invention relates to immunoassays in which the degree of agglutination of reactants is used to indicate the amount of an analyte present in a sample. Agglutination assays have been used for many years in determining the presence or absence of antigens. For example, U.S. Pat. No. 3,171,783 describes the use of agglutination assays for diagnosing pregnancy. More particularly, the invention relates to assays in which agglutination results from the formation of complexes between an antibody for a specific analyte conjugated to a latex particle and another conjugate between the analyte of interest and a carrier molecule. If a sample contains the analyte, it competes with the conjugated analyte and reduces the formation of complexes, thus inhibiting the agglutination. The effect on the degree of agglutination can be measured by absorbance of light in a spectrophotometer. However, the method has disadvantages, for example it is necessary to supply as one of the reagents used in the assay the specific antigen (analyte) which is to be measured. Further, another reagent must contain an antibody specific to the antigen (analyte) to be measured, the antibody also being conjugated to latex particles.

Carrying out agglutination assays requires that an antibody specific to the analyte of interest be obtained, generally by developing such an antibody in an animal and recovering and purifying the antibody for use in an assay. The antibody is conjugated (attached) to latex particles and used as a first component of the assay. The analyte (antigen) which corresponds to the one expected to be in the sample is obtained by a synthetic preparation or by purification from a natural source and then conjugated to a carrier molecule, such as a protein or polymer, and used as a second component of the assay. Since the antigen and the antibody bind together, when the first and second components of the assay are combined, the large complexes described above will be formed. However, when a sample is first mixed with the second component, which contains conjugated analyte, any analyte present in the sample will compete with that in the second component and interfere with the agglutination process. The effect of such interference depends on the amount of the analyte in the sample and it can be determined spectroscopically.

The present invention was discovered unexpectedly, during development of an immunoassay for an analyte (deoxypyridine, Dpd) using the agglutination technique just described. It was found that a non-specific antibody conjugated to latex particles had the ability to combine with an antibody specific to the analyte, resulting in agglutination. This effect was inhibited by the presence of the analyte in the sample and could be measured to determine the amount of the analyte in the sample. It had been expected that agglutination would occur when the analyte conjugated to a carrier combined with the antibody specific to the analyte which had been conjugated to latex particles. However, it was found that the agglutination was occurring even when no analyte was present. Furthermore, the antibody specific to the analyte was binding to a non-specific (generic) antibody, in the absence of the analyte. When the analyte was present in the sample, it interfered with the agglutination in proportion to the amount of the analyte present, making possible a simpler, but similar agglutination assay. As will be seen in the examples below, the new method appears to have general application, since it has been shown to be useable with antibodies from various sources.

Monitoring the presence of pyridinoline and deoxypridinoline has been suggested as a method for determining bone collagen degradation. For example, in U.S. Pat. No. 5,620,861 and U.S. Pat. No. 5,736,344 the amount of an immunocomplex formed between an antibody and pyridinum crosslinks, including the pyridinoline and deoxypridinoline, was measured to indicate the presence of the pyridinum crosslinks. The means used to measure the immunocomplex included the use of a reporter enzyme to produce a colorimetric signal, preferably alkaline phosphatase.

U.S. Pat. No. 4,469,797 discusses a method of monitoring the concentration of digoxin, a drug administered to cardiac patients. It was suggested that various types of immunoassays could be used, including agglutination techniques.

SUMMARY OF THE INVENTION

The invention may be generally described as an improved agglutination immunoassay, in which it is not necessary to include in one of the reacting components a conjugate of the analyte to be determined.

The invention may be described more particularly as comprising the steps of:

acquiring a first reagent comprising a generic antibody conjugated to latex particles, for example an antibody to mouse IgG.

acquiring a second reagent comprising an antibody specific to the analyte to be determined, for example a monoclonal antibody of the analyte.

combining the sample fluid with the first reagent.

adding the second reagent to the combined first reagent and sample.

measuring the degree of agglutination resulting from adding the second reagent to the combined first reagent and sample.

correlating the degree of agglutination with the amount of analyte in the sample.

In one embodiment, the analyte is deoxypyridinoline (Dpd). In another embodiment, the analyte is digoxin. In a third embodiment, the analyte is theophylline.

In another aspect, the invention includes a system for carrying out the above described immunoassay.

DESCRIPTION OF THE PREFERRED EMBODIMENTS

The Unexpected Discovery

In view of the intense interest in tests for measuring bone density, for detection of osteoporosis and certain diseases, immunoassays for the presence of deoxypyridinoline (Dpd) have been developed. For example, see U.S. Pat. No. 5,620,861 discussed above in which a labeled antibody is used to produce a colored response to the presence of Dpd in urine. The present inventors were investigating the possibility of using agglutination techniques for measuring Dpd. They intended to determine the particle size of a generic antibody (i.e not specific to Dpd) conjugated to latex particles by adding Dpd-specific antibodies to the latex conjugated generic antibody. Since the latex conjugated antibody was generic and not specific to Dpd, it was expected that only a monolayer of the Dpd-specific antibodies would be added to the latex particles. Surprisingly, it was found that the Dpd-specific antibodies continued to add to the latex particles, thus creating agglutination where none had been expected. Then, when adding Dpd was found to inhibit the agglutination, an improved assay was discovered to be feasible.

Antibodies

Antibodies useful in the new immunoassay may be obtained from various sources, including those commercially available. The methods of making antibodies are known in the art and are not part of the present invention. While the examples below used anti-mouse IgG (an immunoglobin class) and antibodies from rabbit and goat as the generic antibody conjugated to latex, other sources of similar antibodies could be used, for example, sheep. It was found that the binding of the generic antibody to the antibody to the specific analyte needed to occur at the heavy chain, that is, the Fc portion. A generic antibody specific for the light chain ($Fab_2$ portions) of the antibody did not provide sufficient agglutination response.

The antibodies specific to the analyte being measured will normally be monoclonal antibodies since they provide binding to one specific eptitope on the analyte. Although a polyclonal antibody specific to an analyte has not been tested, it is believed that a response would be found to be similar to that of monoclonal antibodies.

Analytes

In the examples it will be seen that the method of the invention has been demonstrated with deoxypyridinoline, digoxin, and theophylline. However, the invention is not limited to those analytes, but may be used with other analytes of interest in immunoassays, such as hCG and troponin.

Latex Particles

Latex particles are well known in the immunoassay art and are available commercially. They are generally supplied in the form of an aqueous suspension. The particles typically have a diameter of about 1-100 μm and contain reactive moieties which can bind to antibodies to form the first reagent of the invention, latex particles conjugated to generic antibodies.

New Method

The presence of an analyte in a sample is measured by the degree of agglutination occurring when a first reagent comprising a generic antibody conjugated to latex particles is combined with a sample suspected to contain an analyte and then a second reagent comprising an antibody specific to the analyte is added. The degree of agglutination is correlated with the amount of the analyte in the sample. Alternatively, the second reagent can be added first, with the sample added second, although not necessarily with identical results.

Preparation of Latex-Conjugated Antibody to Mouse IgG

A typical preparation of the latex-conjugated antibody to mouse IgG used in the following examples is as follows:

Materials used are:
- 10% latex-COOH (Bangs P0001040CN) having 100 nm particles with 181 ueq/g.
- 25 mM MES (2-N-morpholino) ethane sulfonic acid, pH 6.1—prepared by 500 mL by adding 2.665 gm of MES (Sigma M5283) to 450 mL of water, adjusted to pH 6.1 with 0.1 N NaOH, raise to 500 mL and filter through a 0.22 μm filter.
- 25 mM MOPSO (3-N-morpholino)-2-hydroxy propane sulfonic acid), pH 7.4—prepared by adding 0.2810 gm of MOPSO (Sigma 8389) to 450 mL of water, adjusted to pH 7.4 with 0.1N NaOH, raise to 500 mL and filter through a 0.22 μm filter.
- EDAC (N-(3-dimethylaminopropyl)-N'-ethylcarbodiimide hydrochloride) (10 mg/mL)—prepared by weighing 15.2 mg of EDAC (Sigma E1769) and adding 1.52 mL of water just prior to use.
- BSA (bovine serum albumin) (50 mg/mL)
- 0.5M ethanolamine (Sigma E9508) pH 8.5—prepared by diluting stock 16M ethanolamine 1:32 and adjusting to pH 8.5 with acetic acid.
- Antibody to mouse IgG—derived from rabbit or goat (Pierce 31194 or Sigma).
- Storage Buffer: 0.1M glycine, pH 8.2, 2 mg/mL BSA, 0.05% Triton X-100, 0.17 M NaCl, 0.2% $NaN_3$.

The stock latex was washed by adding 2.2 mL of stock 10% latex particles with 5.0 mL of 25 mM MES, pH 6.1 and centrifuged in a Beckman J2-21 centrifuge, rotor JA-20 at 20,000 rpm for 60 minutes using a 16×76 mm centrifuge tube. The supernatant was discarded and the latex pellet was resuspended into 5 mL MES buffer. Centrifuging was repeated and the supernatant discarded. The latex pellet was resuspended with MES buffer to 2.2 mL, then the mixture was sonicated in an ice bath for 30 seconds and then stored at 5° C. until used.

The stored latex particles was resonicated and the particle size measured (mean 109.3 nm). Absorbance of the sonicated particles is measured at 530 nM and the percent solids determined from a standard curve (88.6 mg/mL or 8.86% solids).

200 μL of the latex particles (20 mg) were added to 800 μl of 25 mM MES, pH 6.1 in an Amicon® Centricon concentrator having a 500,000 mw cut-off. 0.1044 mL of the 10 mg/mL EDAC solution was added. Then the mixture was mixed while rotating at 200 rpm for 90 minutes.

The centricon was taken from the rotator and centrifuged at 5,500 rpm for 50 minutes and the filtrate discarded. 900 μL of the MES buffer was added to the 20 mg latex particles in the centricon and the mixture was sonicated. 200 μg of anti-mouse IgG was added to the latex while vortexing (10 ug antibody/mg latex). The mixture was rotated at 200 rpm for 60 minutes to complete the binding of latex particles to the selected antibody.

20 μL of the 0.5 ethanolamine was added to 20 mg of antibody/latex and rotated at 200 rpm for 20 minutes. Then, 10 μL of the 5% BSA solution was added and the mixture rotated at 200 rpm for 30 minutes. The ethanolamine and BSA serve to block binding sites on the antibody not attached to latex particles.

The excess antibody (unattached) was then washed from the latex particles four times using the 25 mM MOPSO solution. For each wash, 900 μL of the MOPSO solution was added to the centricon concentrator, sonicated, and then centrifuged for 50 minutes at 5,500 rpm. The filtrate was removed after each period of centrifuging and the absorbance measured at 280 nM in order to determine when all excess BSA had been removed.

The latex conjugated antibody pellet resulting from the washing steps was combined with 900 μL of the buffer, sonicated and transferred to a vial. Then, another 900 μL of buffer was added to the Centricon tube, sonicated and transferred to the vial. Sufficient buffer was added to the vial to bring the total to 3 mL and sonicated. The absorbance was measured at 530 nM to determine the latex concentration.

EXAMPLE 1 (COMPARATIVE)

In this example a conventional agglutination protocol is shown to be operative. A Roché Cobas analyzer measuring the degree of agglutination at a wave length of 530 nM and 37° C. was used. 200 μL of a conjugate of latex particles and an antibody to mouse IgG (Fc fraction) was mixed with 25 μL of a sample containing 0 or 200 nM Dpd. Then an antibody to Dpd was added and the absorbance was read to indicate the degree of agglutination which is related to the presence of Dpd. Tests were carried out in which the sample containing Dpd (the analyte) conjugated with Neutravidin:biotin, both with and without latex particles. In the table below, the tests labeled "Double Latex System" refer to those tests in which both the mouse IgG antibody and the sample containing Dpd (the analyte) were conjugated to latex particles. Where the tests are labeled "Single Latex System" the sample containing Dpd was not conjugated to latex particles, but for results labeled R1-9 through R-11 the Dpd was conjugated to neutravidin:biotin. Dpd was not conjugated to a carrier in the results of R1-14 and R1-17. In the later tests the results labeled R1-14 and R1-17 show that when no Dpd (analyte) was present in the sample, agglutination still occurred when the antibody to Dpd was combined with the mouse IgG antibody/latex and that when Dpd was present, agglutination was reduced. When comparing tests R1-9, R1-10, R1-11, and R1-14 it can be seen that the results did not depend on the use of the Neutravidin:biotin carrier or latex particles. Thus, the traditional agglutination assay can be simplified according to the present invention. A generic antibody conjugated to latex particles, when contacted with an antibody specific to the analyte of interest will cause agglutination, and the degree of agglutination will be reduced by the presence of the analyte.

TABLE A

|  | Double Latex System | | | | Single Latex System | | | | |
| --- | --- | --- | --- | --- | --- | --- | --- | --- | --- |
| Test No. | R1-1 | R1-2 | R1-3 | R1-4 | R1-9 | R1-10 | R1-11 | R1-14 | R1-17 |
| avidin: biotin Dpd, p moles[1] 10 sec[5] | 70 | 35 | 17.5 | 8.75 | 7 | 3.5 | 1.75 | 0 | 0 |
| 0 nM[2] Dpd | 0.864 | 0.835 | 0.738 | 0.662 | 0.503 | 0.552 | 0.549 | 0.542 | 0.515 |
| 200 nM[3] Dpd | 0.716 | 0.649 | 0.543 | 0.463 | 0.351 | 0.371 | 0.380 | 0.371 | 0.350 |
| delta (0-200)[4] Dpd 2 min[5] | 0.148 | 0.186 | 0.195 | 0.200 | 0.152 | 0.181 | 0.169 | 0.171 | 0.164 |
| 0 nM[2] Dpd | 0.349 | 0.354 | 0.326 | 0.293 | 0.201 | 0.223 | 0.226 | 0.226 | 0.217 |
| 200 nM[3] Dpd | 0.311 | 0.296 | 0.256 | 0.219 | 0.148 | 0.161 | 0.164 | 0.161 | 0.154 |
| Delta (0-200)[4]"Dpd | 0.037 | 0.057 | 0.070 | 0.074 | 0.053 | 0.062 | 0.062 | 0.064 | 0.063 |

[1]amount of Dpd (analyte) conjugated to avidin: biotin carrier to latex particles in Double Latex System.
[2][3]amount of Dpd present in sample for absorbance reported in mA/min.
[4]difference in absorbance in mA/min.
[5]time of absorbance measurement after addition of antibody to Dpd (<Dpd>).

EXAMPLE 2

In the above tests, the antibody to mouse IgG was indicated to be the Fc fraction of the antibody, as was the antibody to Dpd. In a test similar to those reported as R1-14 and R1-17 above, the antibody to Dpd was not the Fc fraction, but instead the F(ab')$_{(2)}$ fragment. The F(ab')$_2$ fragment is the portion of the antibody which binds to an antigen, while the Fc portion binds to cells of the immune system, e.g. phagocytes, which can destroy the antigen. It was found that the F(ab')$_{(2)}$ fragment of the antibody to Dpd caused no agglutination, in contrast with the results shown in Example 1. It can be concluded that the antibody to the analyte (antigen) should be the Fc portion and that the agglutination is affected by the Fc portion of the antibody to the analyte.

EXAMPLE 3

Another test was carried out similar to those of R1-14 and R1-17 in Example 1, but instead of Dpd as the analyte, pyridinoline (Pyd) was used. It was found that agglutination occurred, but that it was only very little inhibited by Pyd. Thus, it was concluded that the assay of the invention would be useful for measuring the presence of Dpd, but not the related compound Pyd.

EXAMPLE 4

The results of Example 3 were confirmed in another test in which the antibody for Digoxin was used instead of the antibody for Dpd in Example 1. (R1-14 and R1-17). Agglutination was achieved, but adding Dpd as analyte did not inhibit agglutination. Thus, confirming specificity of the assay for Dpd and low non-specific binding.

EXAMPLE 5

Selecting the second method of reporting the change in absorbance used in Example 1, i.e. the difference between 0 and 2 minutes, a test was run to compare the traditional agglutination assay with the assay method of the invention. The three components used in each assay are summarized as follows:

|  | Traditional Assay | Assay of the Invention |
| --- | --- | --- |
| First Component | Latex-antibody to mouse IgG (Fc)<Dpd> | Latex-antibody to Mouse IgG (Fc) |
| Second Component | Neutravidin:biotin-Dpd | Antibody to Dpd (<Dpd>) |
| Sample | Dpd | Dpd |

10 ug of the conjugated mouse IgG and 40 ug of Neutravidin:biotin-Dpd were combined with 5 μg/mg of the antibody to Dpd, i.e. <Dpd> in the traditional assay. In the assay of the invention, 10 ug of the conjugated mouse IgG (Fc) was combined with 5 μg/mg of <Dpd>. The Dpd was added in increasing amounts and the absorbance measured after two minutes. The results are summarized in Table B.

TABLE B

|  | Absorption (cor) | |
| --- | --- | --- |
| Dpd (nM) | Traditional Assay | Invention Assay |
| 0 | 0.2676 | 0.2541 |
| 11 | 0.2662 | 0.2497 |

TABLE B-continued

| | Absorption (cor) | |
|---|---|---|
| Dpd (nM) | Traditional Assay | Invention Assay |
| 36 | 0.2614 | 0.2374 |
| 63 | 0.2514 | 0.2243 |
| 95 | 0.25 | 0.2100 |
| 194 | 0.2299 | 0.1872 |
| 309 | 0.2232 | 0.1737 |

The absorbance change as Dpd is added indicates the inhibition in the agglutination of the latex particles conjugated to the antibody to mouse IgG. It can be seen that the effect on absorbance is significantly greater in the inventive assay compared to the traditional assay.

A more detailed study was carried out on the inventive assay to test its precision. It was found that in the range of 0-200 nM Dpd the coefficient of variation was less than 10%.

EXAMPLE 6

The inventive assay was repeated using digoxin (a therapeutic drug) rather than Dpd. The components used were:
First Component: latex-antibody to mouse IgG (Fc), 10 μg
Second Component: antibody to Digoxin (<digoxin>), 5 μg/mg
Sample: digoxin The assay was repeated substituting Dpd for Digoxin. The results of the tests are given in the following table.

TABLE C

| | Absorbance[1] (cor.) | |
|---|---|---|
| digoxin/Dpd, nM | digoxin | Dpd |
| 0 | 0.0734 | 0.0733 |
| 25 | 0.0733 | 0.0734 |
| 50 | 0.0721 | 0.0726 |
| 100 | 0.0649 | 0.0746 |
| 200 | 0.0611 | 0.0747 |
| 400 | 0.0509 | 0.0754 |
| 800 | 0.0492 | 0.0766 |

[1]after 2 minutes

It can be seen that Dpd did not inhibit agglutination of the Digoxin system, as was true in the use of digoxin in the Dpd system in Example 4. However, the inventive assay was useful in measuring the presence of digoxin when the second component was an antibody to digoxin.

EXAMPLE 7

It has been found that the inhibition of agglutination is affected by the concentration of the antibody to mouse IgG (Fc) conjugated to latex particles An optimum concentration was found in a experiment in which the 10 ug/mg concentration of the antibody to mouse IgG (Fc) typically used in the above examples was diluted by 10, 20 and 40 times. The absorbance change between 0 and 100 nM additions of Dpd (the analyte) were measured and are compared in the table below. The antibody to Dpd was also varied, since its concentration will affect the degree of agglutination. Three concentrations of the Dpd antibody were tested, 5.34, 13.34 and 26.68 μg/mg.

TABLE D

| Dilution | 5.34<Dpd> | 13.34<Dpd> | 26.68<Dpd> |
|---|---|---|---|
| 10X | 16 | 30.6 | 23.5 |
| 20X | 24.5 | 49.6 | 25.8 |
| 40X | 20.7 | 25 | 12.7 |

It can be seen that an optimum dilution of about 20 times the latex/anti-mouse IgG at 13.34 μg/mL of the antibody to Dpd (<Dpd>) provided the maximum change in agglutination inhibition.

EXAMPLE 8

Using the 20 fold dilution of the 10 μg/mg antibody to mouse IgG (Fc) conjugated to latex particles and the 13.34 μg/mL of the antibody to Dpd (<Dpd>) found in Example 7 to provide the optimum inhibition of agglutination, a series of 16 replicates of varying concentrations of Dpd (the analyte). It was found that in general, the coefficient of variation was 10% or less. The exceptions were confined to the lowest concentrations of Dpd.

EXAMPLE 9

The previous examples have reported the results obtained using the latex conjugated antibody to mouse IgG (Fc) obtained from goat and rabbit sources. Further testing of other sources of antibodies to the mouse IgG was carried out and is reported below. The sources used were:

(a) rabbit-derived antibody to mouse IgG (Fc)

(b) rabbit-derived antibody to mouse IgG—duplicate of (a) from different supplier (c) goat-derived antibody to mouse IgG (Fc)

(d) goat-derived antibody to mouse IgG (Fab$_2$)

(e) rabbit-derived antibody to mouse IgG (Heavy and Light chain)

(f) goat-derived antibody to mouse IgG (Heavy chain)

(g) goat-derived antibody to mouse IgG (Fc) absorbed against human serum protein Each of the antibodies (a)-(g) were conjugated to latex particles (10 ug/mL). The concentration of the antibody to Dpd was 13.34 μg/mL. Dpd (the analyte) was added at concentrations between 0 and 309 nM. The absorbance was measured after 0.5 and 120 seconds. The results are given on the following table:

TABLE E

| MAS Standards | | A<br>Rabbit anti-mouse IgG (Fc) | | | B<br>Rabbit anti-mouse IgG (Fc) | | | C<br>Goat anti-mouse IgG (Fc) | | | D<br>Goat anti-mouse IgG (Fab$_2$) | | |
|---|---|---|---|---|---|---|---|---|---|---|---|---|---|
| Level | NM Dpd | 0.5 Sec | 120 Sec. | Delta | 0.5 Sec. | 120 Sec. | Delta | 0.5 Sec. | 120 Sec. | Delta | 0.5 Sec. | 120 Sec. | Delta |
| 1 | 0 | 0.1667 | 0.4963 | 0.3296 | 0.1612 | 0.5261 | 0.3649 | 0.1667 | 0.3350 | 0.1683 | 0.1448 | 0.1721 | 0.0273 |
| 2 | 11 | 0.1682 | 0.4925 | 0.3243 | 0.1605 | 0.5221 | 0.3616 | 0.1655 | 0.3300 | 0.1645 | 0.1476 | 0.1748 | 0.0272 |

TABLE E-continued

| | | | | | | | | | | | | |
|---|---|---|---|---|---|---|---|---|---|---|---|---|
| 3 | 36  | 0.1686 | 0.4736 | 0.3050 | 0.1646 | 0.5145 | 0.3499 | 0.1684 | 0.3204 | 0.1520 | 0.1465 | 0.1706 | 0.0241 |
| 4 | 63  | 0.1674 | 0.4512 | 0.2838 | 0.1641 | 0.5047 | 0.3406 | 0.1655 | 0.2985 | 0.1330 | 0.1460 | 0.1671 | 0.0211 |
| 5 | 95  | 0.1693 | 0.4355 | 0.2662 | 0.1622 | 0.4858 | 0.3236 | 0.1658 | 0.2859 | 0.1201 | 0.1485 | 0.1672 | 0.0187 |
| 6 | 194 | 0.1673 | 0.3873 | 0.2200 | 0.1597 | 0.4415 | 0.2818 | 0.1686 | 0.2631 | 0.0945 | 0.1499 | 0.1627 | 0.0128 |
| 7 | 309 | 0.1661 | 0.3683 | 0.2022 | 0.1694 | 0.4400 | 0.2706 | 0.1704 | 0.2562 | 0.0858 | 0.1472 | 0.1588 | 0.0116 |

| MAS Standards | | E Rabbit anti-mouse IgG (H&L) | | | F Goat anti-mouse IgG (H) | | | G Goat anti-mouse IgG (Fc) Absorbed | | |
|---|---|---|---|---|---|---|---|---|---|---|
| Level | NM Dpd | 0.5 Sec | 120 Sec | Delta | 0.5 Sec. | 120 Sec. | Delta | 0.5 Sec. | 120 Sec. | Delta |
| 1 | 0   | 0.1755 | 0.4735 | 0.2980 | 0.1625 | 0.3915 | 0.2290 | 0.1662 | 0.2949 | 0.1287 |
| 2 | 11  | 0.1760 | 0.4705 | 0.2945 | 0.1626 | 0.3904 | 0.2278 | 0.1620 | 0.2899 | 0.1279 |
| 3 | 36  | 0.1782 | 0.4585 | 0.2803 | 0.1631 | 0.3707 | 0.2076 | 0.1606 | 0.2750 | 0.1144 |
| 4 | 63  | 0.1791 | 0.4416 | 0.2625 | 0.1654 | 0.3571 | 0.1917 | 0.1639 | 0.2666 | 0.1027 |
| 5 | 95  | 0.1767 | 0.4236 | 0.2469 | 0.1606 | 0.3307 | 0.1701 | 0.1622 | 0.2544 | 0.0922 |
| 6 | 194 | 0.1776 | 0.3896 | 0.2120 | 0.1638 | 0.2996 | 0.1358 | 0.1625 | 0.2353 | 0.0728 |
| 7 | 309 | 0.1744 | 0.3626 | 0.1882 | 0.1656 | 0.2834 | 0.1178 | 0.1645 | 0.2295 | 0.0650 | mA change of level 1 to level 7

| | mA |
|---|---|
| A | 127.4 |
| B | 94.3 |
| C | 82.5 |
| D | 15.7 |
| E | 109.8 |
| F | 111.2 |
| G | 63.7 |

It can be seen that source of the antibody to mouse IgG was not critical to the results, but that the portion of the antibody used can be significant, as shown in D where the $Fab_2$ portion did not agglutinate. There was significant differences in the change of absorption among the samples.

EXAMPLE 10

It was found that when the method of the invention was used to monitor the presence of theophylline in human serum that the human serum appeared to be affecting the agglutination. In that experiment, latex conjugated with 10 μg of rabbit-derived antibody to mouse IgG (Fc) was combined with a monoclonal antibody to theophylline and three known concentrations of theophylline in human serum (Chiron).

Further investigation of the effect of human serum was carried using the rabbit-derived antibody to mouse IgG (Fc) and a monoclonal antibody to theophylline. Serum free of theophylline was tested and then diluted with serum to determine if serum was the cause of the results found with theophylline in serum. The results are shown in the following table.

TABLE F

| Sample | Absorbance after 2 minutes ($\times 10^3$) |
|---|---|
| Buffer[1] | 96.6 |
| Serum[2] | 11.7 |
| Serum (1:2) | 17.3 |
| Serum (1:4) | 22.3 |
| Serum (1:8) | 27.2 |
| Serum (1:16) | 39.3 |
| Serum (1:32) | 57.5 |
| Serum (1:64) | 74.0 |
| Serum (1:128) | 83.9 |
| Serum (1:256) | 89.8 |
| Serum (1:512) | 95.2 |

[1]200 mm phosphate buffer pH 7.4
[2]human serum from a single donor

It is evident from the above table that serum was strongly inhibiting agglutination. After the serum was diluted at a ratio of 1:512 with the buffer solution, the effect of the serum was substantially eliminated.

Thereafter, a sample of serum was filtered through Centricon filters which cut off molecules below 10,000, 100,000 and 500,000 molecular weight. These filtered serum samples were then compared with unfiltered serum in a similar assay, with the following results:

TABLE G

| Serum | Absorbance after 2 minutes ($\times 10^3$) |
|---|---|
| None | 396.6 |
| Below 10,000 mw | 401.0 |
| Below 100,000 mw | 402.0 |
| Below 500,000 mw | 250.9 |
| Unfiltered | 78.4 |

Since the serum samples in which molecules above 10,000 and 100,000 molecular weight did not affect agglutination significantly, while the samples containing molecules below 500,000 mw inhibited agglutination, it was concluded that the molecules in serum above about 100,000 mw were responsible for the inhibiting effect.

EXAMPLE 11

A set of 87 clinical urine samples were tested using the 10 ug/mL of rabbit-derived antibody to mouse IgG (Fc) conjugated to latex particles and 13.34 μg/mL of the antibody to Dpd. The results were compared to those obtained using the Bayer Immuno-1™ Auto Analyzer (Dpd Assay). While the results were directionally similar, the statistical correlation was only about 50%, although removing four outlying values improved the correlation to 85%.

What is claimed is:
1. A system for determining the presence of an analyte in a sample by agglutination of particles consisting essentially of:

(a) a first reagent comprising of a non-specific antibody to Ig antibodies conjugated to latex particles;

(b) a second reagent comprising of an antibody specific to said analyte, which reagent is capable of causing agglutination of the latex particles of (a) when said first and second reagents are combined, said non-specific antibody binding at the Fc portion of said antibody specific to said analyte;

(c) a means for measuring the amount of light at a predetermined wavelength absorbed by agglutination of said latex particles of (a) when said first and second reagents are combined with said sample, thereby determining the presence of an analyte in said sample and permitting correlation of the degree of said agglutination in inverse proportion to the amount of said analyte in said sample.

2. The system of claim 1 wherein said antibody specific to said analyte is an antibody to deoxypyridinoline (Dpd).

3. The system of claim 1 wherein said antibody specific to said analyte is an antibody to digoxin.

4. The system of claim 1 wherein said antibody specific to said analyte is an antibody to theophylline.

5. The system of claim 1 wherein said non-specific antibody is an antibody to mouse IgG.

6. The system of claim 5 wherein said non-specific antibody is the Fc portion of mouse IgG.

7. The system of claim 5 wherein said antibody to mouse IgG is derived from rabbits.

8. The system of claim 5 wherein said antibody to mouse IgG is derived from goats.

9. The system of claim 1 wherein said antibody specific to said analyte is a monoclonal antibody.

* * * * *